(12) United States Patent
Baid

(10) Patent No.: US 10,307,572 B2
(45) Date of Patent: *Jun. 4, 2019

(54) NEEDLE SAFETY DEVICE

(71) Applicant: Poly Medicure Limited, Faridabad, Haryana (IN)

(72) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,419

(22) Filed: Aug. 26, 2016

(65) Prior Publication Data

US 2017/0007804 A1    Jan. 12, 2017

Related U.S. Application Data

(63) Continuation of application No. 14/237,657, filed as application No. PCT/IB2012/054034 on Aug. 8, 2012, now Pat. No. 9,427,555.

(30) Foreign Application Priority Data

Aug. 9, 2011 (IN) ............................ 2330/DEL/2011

(51) Int. Cl.
*A61M 25/06* (2006.01)
*A61M 5/32* (2006.01)

(52) U.S. Cl.
CPC ...... *A61M 25/0631* (2013.01); *A61M 5/3273* (2013.01); *A61M 25/0618* (2013.01); *A61M 2005/325* (2013.01)

(58) Field of Classification Search
CPC ............ A61M 25/0631; A61M 5/3273; A61M 25/0618; A61M 2005/325
See application file for complete search history.

(56) References Cited

U.S. PATENT DOCUMENTS 4,838,880 A    6/1989  Honma
9,427,555 B2 *  8/2016  Baid .................... A61M 5/3273
(Continued)

FOREIGN PATENT DOCUMENTS

DE    20 2007 009 97 U1    11/2007
EP         2 016 963 A1     1/2009
(Continued)

*Primary Examiner* — Amber R Stiles
(74) *Attorney, Agent, or Firm* — Bodi Law LLC

(57) ABSTRACT

The invention relates to a needle safety device for a medical device, the needle safety device comprising: a base portion having a bore extending along a longitudinal center axis therethrough for receiving a needle; and two opposing jaws extending from the base portion generally in the axial direction and each having a head portion in the region of its free end, wherein the needle safety device includes a locking projection for securing the needle safety device to the medical device. The needle safety device according to the invention further provides at least one elastic element mounted to the jaws in a non-surrounding manner lateral to the center axis in a region between the base portion and the head portions, wherein at least one elastic element and the jaws are configured such that the jaws can be spread apart against a restoring force of at least one elastic element in order to allow the needle received in the bore to extend all the way through the needle safety device.

24 Claims, 8 Drawing Sheets

(56) References Cited

U.S. PATENT DOCUMENTS

| | | |
|---|---|---|
| 2009/0292248 A1 | 11/2009 | Schon et al. |
| 2010/0222749 A1* | 9/2010 | Baid .................. A61M 5/3273 604/263 |
| 2012/0035552 A1 | 2/2012 | Woehr |

FOREIGN PATENT DOCUMENTS

| | | |
|---|---|---|
| EP | 2 127 692 A1 | 12/2009 |
| GB | 2451153 B | 2/2011 |
| WO | 92 22344 | 12/1992 |
| WO | 2012016660 A1 | 2/2012 |

* cited by examiner

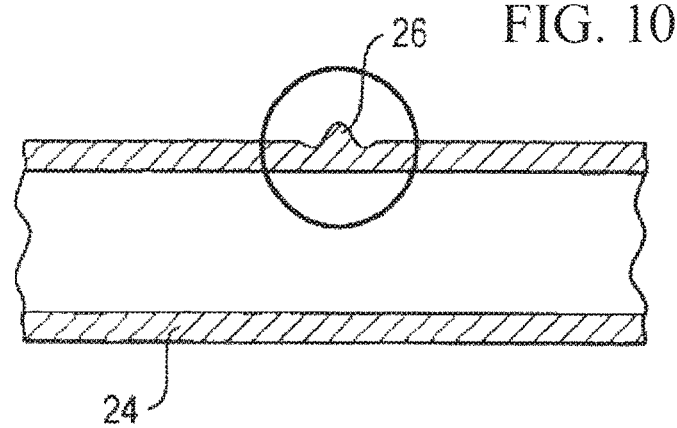
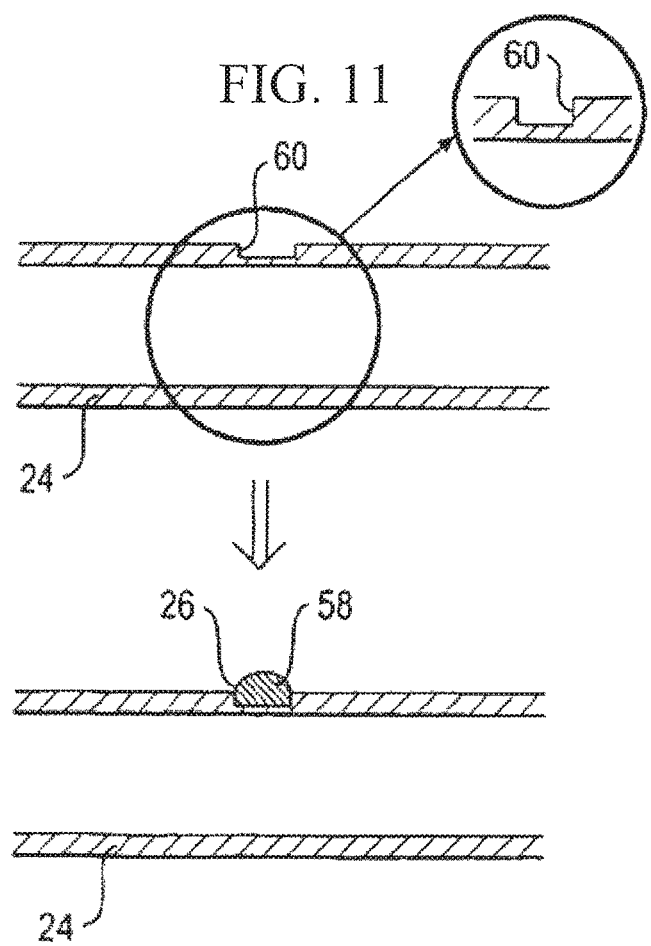

NEEDLE SAFETY DEVICE

CROSS REFERENCES TO RELATED APPLICATIONS

This application is a continuation of U.S. patent application Ser. No. 14/237,657 filed on Feb. 7, 2014, which is the national phase of International Application No. PCT/IB2012/054034 filed on Aug. 8, 2012, which claims priority from Indian Provisional Patent Application No. 2330/DEL/2011 dated Aug. 9, 2011, the entire disclosures of which are incorporated herein by reference.

The present invention relates to a needle safety device for a medical device such as, for example, an intravenous catheter apparatus, a base portion having a bore extending along a longitudinal center axis therethrough for receiving a needle; and two opposing jaws extending from the base portion generally in the axial direction and each having a head portion in the region of its free end, wherein the needle safety device includes a locking projection for securing the needle safety device to the medical device.

A needle safety device of this kind is generally known and operative as a guard for the tip of a needle of the medical device by automatically covering the needle tip during withdrawal of the needle from a patient. The needle safety device thereby serves to prevent accidental pricking of for example, a medical professional by the needle after removal of the needle from the medical device.

In the prior art document EP 2 016 963 B1 a corresponding needle safety device is disclosed. This corresponding safety device has an annular resilient member surrounding the two jaws in a ring-like fashion. Although this needle safety device has a reliable functioning, it can be improved and simplified in regard to its structure.

It is an object of the invention to provide a needle safety device which provides a reliable protection against accidental pricking by the needle and which has a simple structure.

This object is satisfied by a needle safety device having the features of claim 1.

The needle safety device of the invention is characterized by at least one elastic element mounted to the jaws in a non-surrounding manner lateral to the center axis in a region between the base portion and the head portions, wherein the at least one elastic element and the jaws are configured such that the jaws can be spread apart against a restoring force of the at least one elastic element in order to allow the needle received in the bore to extend all the way through the needle safety device.

Due to the at least one elastic element exerting its restoring force on the jaws in the spread apart state of the jaws, which is the state in which the medical device, for example, an intravenous catheter apparatus, is typically shelved prior to use, the at least one elastic element ensures that the spread apart jaws will snap together and guard the needle tip upon withdrawal of the needle from the medical device even after a longer shelf time, thereby continuously ensuring a correct functioning of the needle safety device. In addition, the at least one elastic element prevents the jaws from becoming loose when the needle safety device slides along the needle, thereby further aiding a correct functioning of the needle safety device.

As a result of the at least one elastic element being arranged in a region between the base portion and the head portions of the jaws, the at least one elastic element also helps prevent the needle tip from protruding sideways out of the needle safety device, thereby further increasing the protecting function of the needle safety device.

Furthermore, due to the arrangement of the at least one elastic element between the base portion and the head portions of the jaws, a locking recess for receiving a locking protrusion formed inside the housing of the medical device is formed between the elastic element and the locking shoulder of the at least one head portion. When the locking protrusion engages with the recess formed by the shoulder of the at least one head portion and the at least one elastic element, the needle safety device is safely secured inside the housing of the medical device and is, in particular, prevented from in the axial direction relative to the housing.

In contrast to the above-mentioned prior art, the at least one elastic element does not surround the needle safety device. Instead, the at least one elastic element is mounted to the jaws such that it biases the jaws to one another by means of the restoration force. Preferably the at least one elastic element is integrally fixed to the jaws such that it cannot be moved or lost or inappropriately positioned on the needle safety device in use or during manufacturing.

According to one embodiment, the at least one elastic element provides said restoring force substantially in axial direction. In other words, the at least one elastic element is drawn or tensioned substantially along the direction of the longitudinal center axis of the needle safety device, i.e. along the needle shaft when the needle shaft extends through the space between the two jaws and spreads the jaws under the restoration force of the at least one elastic element.

According to an alternative embodiment, the at least one elastic element provides said restoring force transverse to said axial direction. In this alternative embodiment, the at least one elastic element is drawn or tensioned substantially transverse to the direction of the longitudinal center axis of the needle safety device, i.e. in the direction transverse to the needle shaft when the needle shaft extends through the space between the two jaws and spreads the jaws apart against the restoration force of the at least one elastic element.

In a further embodiment, the two different kinds of elastic elements can be combined, e.g. by using one elastic element providing its restoration force transverse to said axial direction on one side of the needle shaft and providing its restoration force substantially along the axial direction on the other side of the needle shaft.

The at least one elastic element can be adapted to form a partial sidewall such that together with the jaws it defines a chamber inside the needle safety device, in which the needle tip is held after complete withdrawal of the needle from the medical device, thereby further increasing the guarding function of the needle safety device.

The axial dimension of the at least one elastic element may range from about one fifth of the length of the jaws to about two thirds or three fourths of the length of the jaws, and preferably is in the range of about one third of the length of the jaws.

Preferably, the at least one elastic element is made from a material having elastic properties, for example, an elastic material such as rubber, silicone or the like. Due to its elastic properties, the elastic element creates a restoring force on the jaws, when the needle fully extends through the needle safety device thereby spreading the jaws apart and expanding the elastic element. As soon as the needle tip passes the free ends of the jaws upon pulling the needle through the needle safety device, the jaws are positively collapsed by the elastic element due to its restoring force. As described below, it can also be formed by a metal spring. For example, the at least one elastic element comprises a tension ring or tension strip or tension spring mounted to the jaws, respectively.

In accordance with a further embodiment, the jaws are connected to each other by at least one link in a region between the base portion and the head portions. Preferably, the link is arranged in the region of the elastic element. The link may be provided on only one side of the jaws. Alternatively, first and second links may be provided on opposite sides of the jaws.

Preferably, the at least one link is formed to have spring-like properties such that the jaws can be spread apart against a restoring force of the link. For example, the link may have a curved shape, such as an S- or Z-like shape. Alternatively, the link may have a substantially straight shape.

The at least one link prevents the two jaws from spreading apart too far, thus preventing over-stretching of the elastic element which could result in a loss of elastic properties. Furthermore, the link supports the elastic element in exerting a force on the jaws in the collapsing direction, thereby aiding the elastic element in preventing the jaws from becoming loose when the needle safety device slides along the needle. In addition, the link causes the jaws to collapse even if the elastic element should fail in its function. The link is designed such that it retains its spring-like properties over the period of shelf live.

To allow for a simplified and cost-effective production of the needle safety device, the base portion, the jaws, the elastic element and preferably also the at least one link may be integrally formed and preferably made from a plastic material, for example, by injection molding. Alternatively, the base portion, the jaws, and preferably also the at least one link may be made from a metal material. According to a further embodiment, the base portion, the jaws and/or the link each comprise a different material or combination of materials, such as a different plastic material, a different metal material or a different combination of plastic and/or metal materials. For example, the base may be made from a metal material and the jaws may be made from a plastic material, or vice versa. It is also considered that the inner part of the jaws, which contacts the needle, is made from a thermoplastic material such as TPE, whereas the outer part of the jaws may be made from a different material, for example, a plastic, metal, composite or elastomer material, so that the needle safety device causes less friction when sliding along the needle thereby facilitating the withdrawal of the needle. The elastic element can be formed of any kind of rubber material.

In regard to the further structure of the needle safety device according to the present invention, it is possible according to one embodiment that the tension ring is mounted to mounting features provided on each of the jaws. In particular, in this embodiment of the invention it can be provided that the mounting features comprise mounting projections, mounting hooks, mounting recesses or the like. This means that the tension ring is hooked onto the particular mounting features and biased therebetween.

As an alternative, it is possible that the tension strip is integrally fixed with its ends to the jaws, in particular by using an adhesive or by co-molding. In other words, the tension strip is fixedly connected with it ends to each of the jaws and connects the jaws such that the tension strip is biased as soon as the jaws are spread by the needle shaft.

According to a still further embodiment, it can be provided that tension spring is formed by a coil spring fixed with its ends to each of the jaws, respectively. The coil spring is extended against its restoration force when the jaws are spread by the needle shaft.

Generally, it is possible that only one elastic element is provided on only one side of the jaws. As long as the elastic element is strong enough to provide sufficient restoration force to the jaws, only one elastic element is sufficient. Preferably in order to increase the reliability of the needle safety device according to the present invention first and second elastic elements are provided on opposite sides of the jaws.

In order to prevent the needle tip guarded by the needle safety device from protruding beyond the free ends of the jaws, at least one of the jaws has an angled end section at its free end, which extends towards the other one of the jaws in a direction generally perpendicular to the axial direction.

Preferably, the length of the at least one angled end section is selected such that the angled end section is supported on the needle when the needle extends all the way through the needle safety device, thereby spreading the jaws apart far enough for the shoulder of the head portion of the jaw having the angled end section to be able to engage behind the locking protrusion provided in the housing of the medical device.

The needle safety device according to the present invention as mentioned above has a locking projection for securing the needle safety device to the medical device. This locking projection can be formed by a projection which interacts with a corresponding recess or projection in the interior of the medical device, e.g. a catheter hub, which receives the needle safety device. On the other hand, according to an alternative embodiment of the present invention, the locking projection may be formed on an additional arm provided at the needle safety device which interacts with the outside surface of the medical device, e.g. the catheter hub.

Further subject matter of the invention is a needle for a medical device such as, for example, an intravenous catheter apparatus, which has an inner profile, i.e. cross-section area defined by the inner periphery or circumference of the needle, a principal outer profile, i.e. principal cross-section area defined by the outer periphery or circumference of the needle, and a needle tip, the needle further comprising at least one enlargement in the region of the needle tip, wherein the enlargement is formed from an increase of the outer profile, whereas the inner profile remains substantially unchanged.

Still further subject matter of the invention is a medical device, in particular an intravenous catheter apparatus, comprising a needle of the aforementioned type and a needle safety device, in particular of the above described kind, which is slidably arranged on the needle for protecting the needle tip, wherein the needle safety device includes a base portion having a bore extending therethrough for receiving the needle, the bore being adapted to the principal outer profile of the needle.

The enlargement and thus increase in effective diameter in the region of the needle tip prevents the needle tip from being pulled through the base portion of the needle safety device during withdrawal of the needle from the medical device. In other words the enlargement prevents the needle safety device from sliding beyond the needle tip and thus ensures that the needle tip is continuously and reliably guarded by the needle safety device after removal of the needle from the medical device.

By forming the enlargement such that only the outer profile of the needle is increased, whereas the inner profile remains unchanged, in other words by maintaining a substantially constant inner cross-section area throughout the entire length of the needle, blood from a patient entering the needle can freely flow along the inside of the needle. In other words a flashback of blood, which occurs when the needle penetrates a vein, is not adversely affected by the enlargement.

The enlargement may be formed by subjecting the needle to concentrated heat at a localized area using, for example, a welding process such as a laser welding process, with or without addition of additional material.

Alternatively, the enlargement may be formed from additional material dispensed onto the outer surface of the needle. In order to locate the dispensed material in a defined position, a recess or groove may be formed in the outer surface or circumference of the needle.

The additional material may, for example, be selected from at least one of a plastic material, an adhesive, a resin and a metal material.

In the case of the additional material being a metal material, the enlargement may, for example, be formed by build-up welding of the additional material onto the needle.

Preferred embodiments of the invention are described in the following description and in the accompanying drawings, wherein:

FIG. 10 shows a cross-sectional view of the needle of FIG. 9 in the region of the enlargement which has been formed by welding; and FIG. 11 shows cross-sectional views of the needle of FIG. 9 in the region of the enlargement, illustrating the formation of the enlargement by a deposition process.

Figure 1:
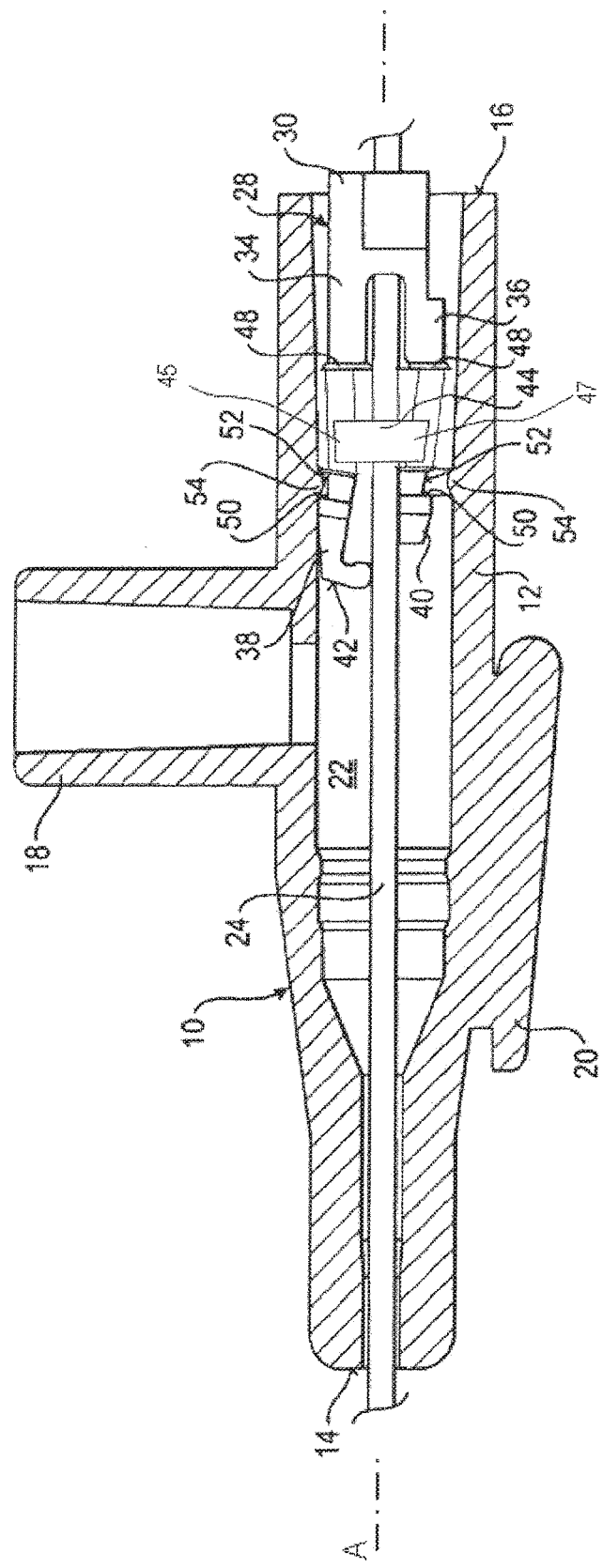
FIG. 1 shows a view partly in cross-section of a wing housing of an intravenous catheter apparatus, including a needle safety device according to a first embodiment of the invention inserted therein and a needle extending therethrough.

Referring to FIG. 1, a catheter hub or wing housing 10 of an intravenous catheter apparatus is shown. The wing housing 10 comprises a main body 12 of generally tubular form and extending in an axial direction. The main body has a distal end 14 and a proximal end 16. A catheter 17 (FIG. 7) is attached to the main body 12 at the distal end 14 of the main body 12. A port 18 extends from the main body 12 in a direction generally perpendicular to the axial direction.

Wings 20 (FIG. 7) are provided at the main body 12 opposite from the port 18. The main body 12 defines a chamber 22 extending from the proximal end 16 towards the distal end 14.

Prior to use of the intravenous catheter apparatus, a needle 24 extends through the wing housing 10 in the axial direction. The needle 24 has an inner profile, i.e. cross-section area defined by the inner periphery or circumference of the needle 24, which is substantially constant across the length of the needle 24. A principal outer profile, i.e. principal cross section area defined by the outer periphery or circumference of the needle 24, is also substantially constant across the length of the needle 24 except for an enlargement 26 of the needle 24 provided in the region of the needle tip at the distal end of the needle 24, which will be described in more detail below with reference to FIGS. 9 to 11.

Still referring to FIG. 1, a needle safety device 28 is slideably arranged on the needle 24. Prior to use of the intravenous catheter apparatus, the needle safety device 28 is inserted into the chamber 22 from the proximal end 16 of the main body 12.

Figure 2:
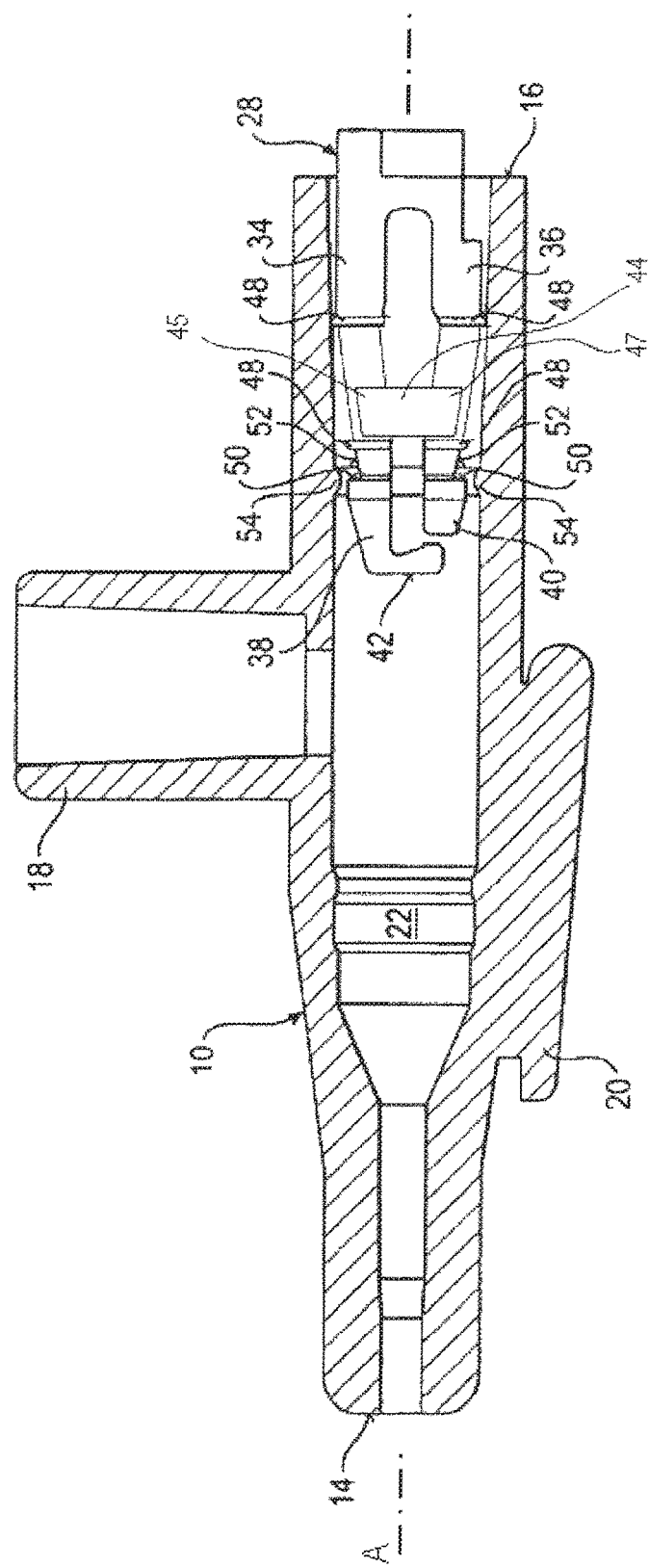
FIG. 2 shows a view partly in cross-section of the wing housing of FIG. 1, including the needle safety device, but not the needle.

As can be seen from FIGS. 1 and 2, the needle safety device 28 comprises a base portion 30 which has a bore extending in the axial direction therethrough for receiving the needle 24. The bore is matched in shape and size to the principal outer profile of the needle 24. The bore can be reinforced with an additional member, like a metal washer, a sleeve or the like. There can also be provided a sleeve on the needle shaft having a larger outer diameter than the bore in the base portion 30.

First and second jaws 34, 36 extend from the base portion 30 generally in the axial direction. The first jaw 34 has a first head portion 38 in the region of its free end, and the second jaw 36 has a second head portion 40 in the region of its free end. The first head portion 38 extends beyond the second head portion 40 and has an angled end section 42 at its free end, which extends towards the second jaw 36 in a direction generally perpendicular to the axial direction.

The length of the angled end section 42 is selected such that the angled end section 42 protrudes over at least a part of the second head portion 40, when the jaws 34, 36 are in a relaxed position as is shown in FIGS. 2 to 6. When the needle 24 extends all the way through the needle safety device 28, such as prior to use of the intravenous catheter device as shown in FIG. 1, the angled end section 42 is supported on the needle 24, whereby the first jaw 34 is forced away from the second jaw 36 from its relaxed position into a spread apart position.

In the embodiment according to FIGS. 1 and 2 the jaws 34, 36 are connected by two tension strips 44 (only one shown) in a region between the base portion 30 and the head portions 38, 40. The tension strips 44 are made from an elastic material, such as rubber, silicone or the like. The tension strips 44 are fixed with their end portions 45, 47 to two opposite sides of the jaws 34, 36, i.e. by using an adhesive or by molding these tensions strips integrally onto the jaws 34, 36. The tension strips 44 exert a restoring force on the jaws 34, 36, when the jaws are spread apart by the needle 24, as shown in FIG. 1. There is no additional elastic member surrounding the needle safety device 28, like a rubber ring or the like.

Figure 3:
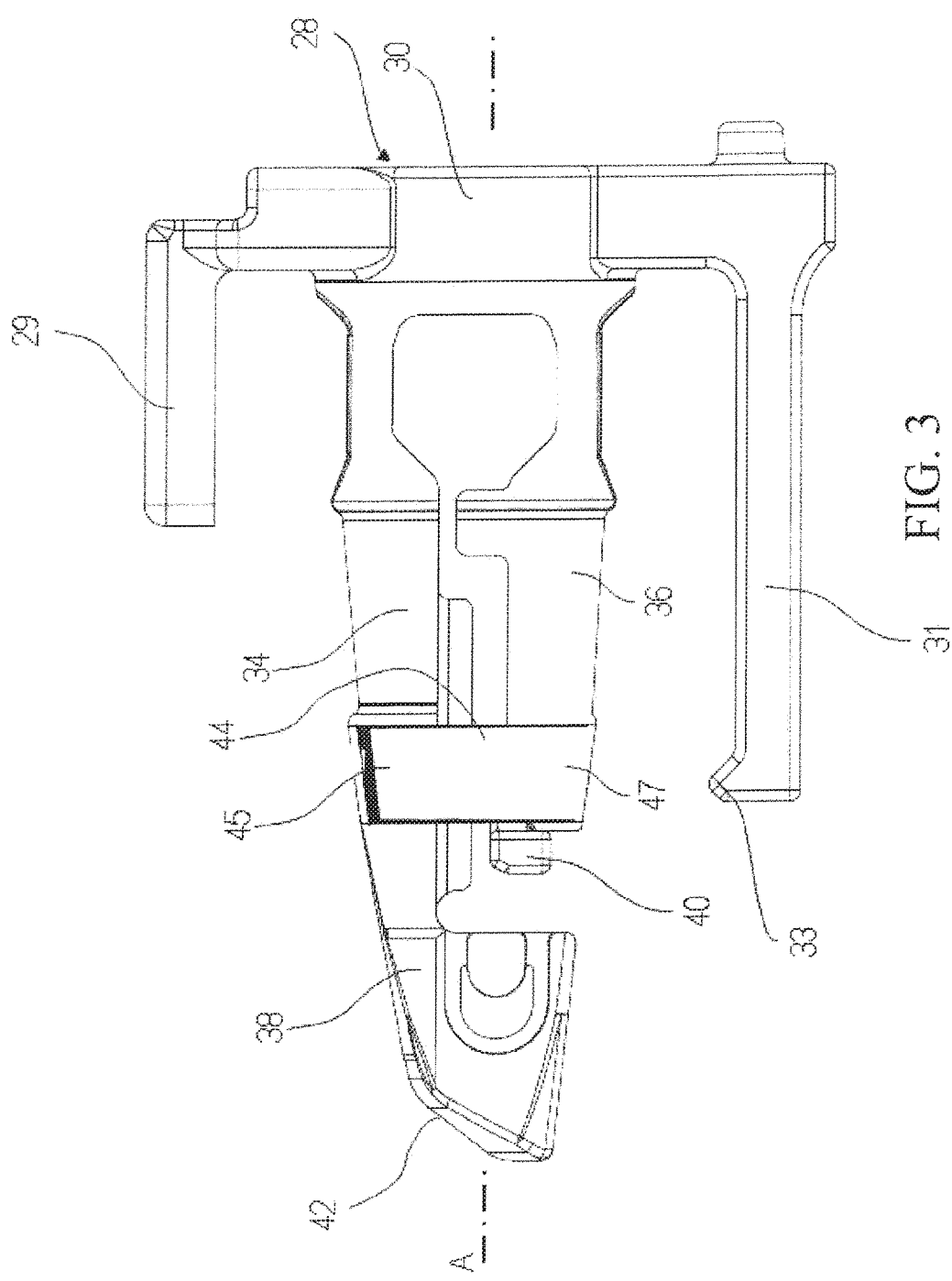
FIG. 3 shows a side view of a second embodiment of the needle safety device including a tension strip biased in a direction transverse to the longitudinal direction.

As is illustrated in FIGS. 1, 2 and 3, the tension strips 44 cover a substantial part of the jaws 34, 36 seen in the axial direction. Specifically, the axial dimension of the tension ring may range from about one fifth of the length of the jaws to about two thirds or three fourth of the length of the jaws, and preferably is in the range of about one third of the length of the jaws.

As can be seen from FIGS. 1 and 2, the jaws 34, 36 are slightly angled towards each other in the region of the tension strips 44, resulting in the outer profile of the needle safety device 28 being tapered towards the head portions 38, 40.

Two part annular protrusions 48 are formed on the outer surface of the jaws 34, 36, as shown in FIGS. 1 and 2. It is to be noted that the part annular protrusions 48 are optional, i.e. the needle safety device 28 can also be made without any part annular protrusions.

As can be seen from FIGS. 1 and 2, a locking shoulder 50 is formed at the side of each head portion 38, 40 facing the tension ring 44. The locking shoulder 50 and the tension ring 44 together form a recess or groove 52.

Referring again to FIG. 1, an annular locking protrusion 54 is formed on the inner surface of the main body 12 of the wing housing 10 and protrudes into the chamber 22.

Prior to use of the intravenous catheter apparatus, i.e. when the needle safety device 28 is inserted into the chamber 22 and the needle 24 extends all the way through the needle safety device 28 and the wing housing 10, the annular locking protrusion 54 is received in the recess 52 defined by the tension ring 44 and the head portion 38 of the first jaw 34, which is forced away from the second jaw 36 due to the angled end section 42 supported on the needle 24.

Because of the annular locking protrusion 54 engaging into the recess 52 of the needle safety device 28 in the spread apart state of the jaws 34, 36, the needle safety device 28 is secured against movement relative to the main body 12 in the axial direction. Specifically, the needle safety device 28 cannot be pulled out of the wing housing 10, since the locking shoulder 50 of the head portion 38 of the first jaw 34 engages behind the annular locking protrusion 54.

Figure 7:
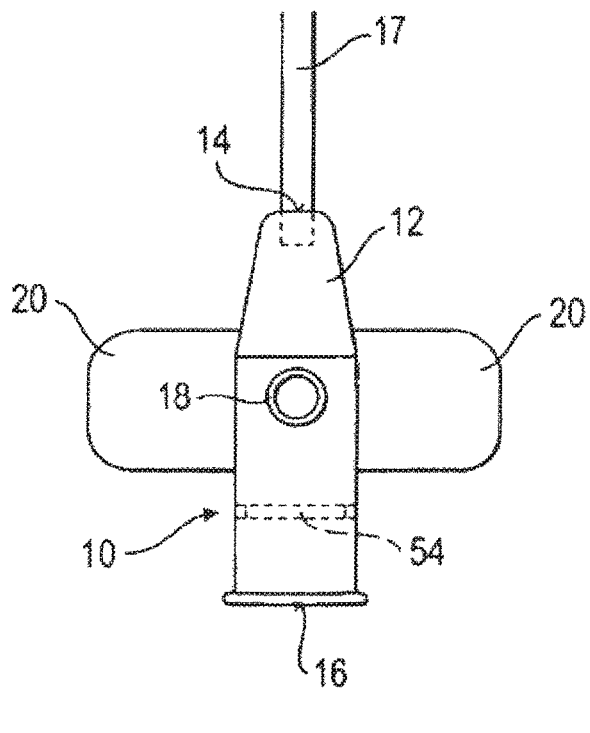
FIG. 7 shows a plan view of the wing housing of FIG. 1.

As is illustrated in FIG. 7, the annular locking protrusion 54 is a distance away from the proximal end 16 of the main body 12, this distance being in the range of 5 mm to 6 mm or more.

Figure 8A:
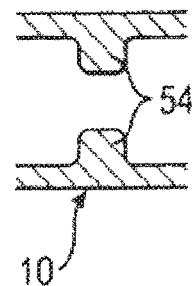
FIG. 8A shows a cross-sectional view of a section of the wing housing of FIG. 7 detailing an annular locking protrusion.
Figure 8B:
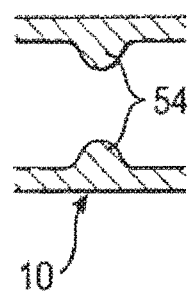
FIG. 8B shows a cross-sectional view of a section of the wing housing of FIG. 7 detailing an alternative embodiment of the annular locking protrusion.

The annular locking protrusion 54 may have a substantially rectangular profile with rounded edges (FIG. 8A), a rounded profile similar to a Gaussian curve or a semi-sinusoidal curve (FIG. 8B) or any other profile suitable for locking of the needle safety device 28 in the wing housing 10.

Preferably, the locking protrusion 54 is of continuous annular shape. However, it is generally also possible to consider an annular locking protrusion 54 having one or more interruptions.

When the needle 24 is being withdrawn from a patient and, thus, from the intravenous catheter apparatus, the needle 24 is simultaneously pulled through the needle safety device 28. As has been mentioned above, as long as the jaws 34, 36 are in their spread apart position, the needle safety device 28 is secured against axial movement relative to the main body 12, i.e. the needle safety device 28 remains in the wing housing 10.

However, as soon as the tip 56 of the needle 24 moves into the needle safety device 28, i.e. passes beyond the angled end section 42 of the first jaw 34, the first jaw 34 snaps back or collapses into its relaxed position, as shown in FIG. 2, due to the restoring force exerted by the tension strip 44.

When the first jaw 34 adopts its relaxed position, the locking protrusion 54 is released from the recess 52 and the locking shoulder 50 of the first head portion 38 is disengaged from the locking protrusion 54. As a result, the safety device 28 is free to move relative to the main body 12 in the axial direction. Specifically, the needle safety device 28 can now be pulled out of the wing housing 10, as is indicated in FIG. 2.

Figure 9A:
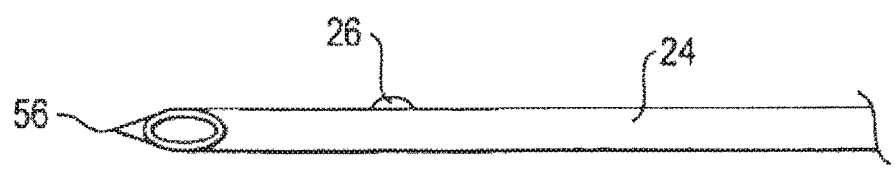
FIG. 9A shows a side view of the needle tip region of the needle of FIG. 1 showing the details of an enlargement formed on the outer surface of the needle.
Figure 9B:
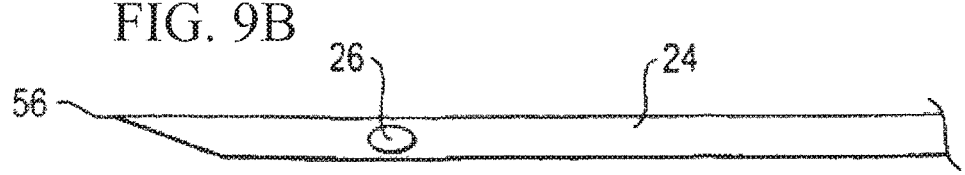
FIG. 9B shows a plan view of the needle tip region of FIG. 9A.

As is illustrated in FIG. 9, the position of the enlargement 26 formed on the outer surface of the needle 24 is selected such that the enlargement 26 abuts the base portion 30 of the needle safety device 28 as soon as the needle tip 56 has passed the free end of the second jaw 36.

Since the maximum outer dimension of the needle 24 in the region of the enlargement 26 is larger than the dimension of the bore in the base portion 30, which is adapted to the principal outer profile or circumference of the needle 24, the needle 24 cannot be further pulled out of the needle safety device 28. In other words, because of the enlargement 26, the needle safety device 28 cannot slide off the needle 24 during normal use of the needle 24 and needle safety device 28, i.e. unless an excessive external force is applied to the needle 24 and/or the needle safety device 28.

With the needle tip 56 captured inside the needle safety device 28, the needle tip 56 is covered by the angled end section 42 of the first jaw 34. At the same time, the tension strips 44 prevent the needle tip 56 from coming sideways out of the needle safety device 28. Hence, the needle tip 56 is safely guarded by the needle safety device 28.

Referring to FIGS. 10 and 11, the enlargement 26 of the needle 24 is formed such that the inner profile of the needle 24 is not affected by the formation of the enlargement 26, i.e. remains substantially unchanged. Thereby, when the needle 24 penetrates a vein, the flow of blood through the needle 24 will not be adversely affected by the enlargement 26.

The enlargement 26 may be formed as a bump by subjecting the needle 24 to concentrated heat at a localized area, for example, using a welding process, such as a build-up welding process or a laser welding process, with or without addition of additional material (FIG. 10).

Alternatively, the enlargement 26 may be formed by dispensing additional material 58 onto the outer surface of the needle 24, such as an adhesive, a resin or a metal material. The additional material 58 may be placed in a recess 60 which has been formed in the outer surface of the needle 24 prior to dispensing the additional material 58. However, formation of the recess 60 is optional.

Although only one enlargement 26 is shown in FIGS. 9 to 11, it is to be noted that more than one enlargement may be present on the outer surface of the needle 24.

Referring to FIG. 3 a second embodiment is shown, wherein the needle safety device 28 is depicted in a relaxed state without the needle) and with a different kind of base portion 30. The base portion includes two arms and 29, 31, wherein the first arm 29 has a shorter extent in axial direction entering the second arm 31 has a larger extent in axial direction. At the free end of the second arm 31 a locking protrusion 33 is integrally formed with the second arm 31 which is provided to interact with a corresponding recess or projection at the outside surface of the wing housing (not shown). Thereby, the needle safety device can be held in position in regard to the wing housing when the needle is been retracted as described above. As soon as the enlargement 26 of the needle comes into contact with the base portion 30, the needle safety device can be retracted from the wing housing by overcoming the resistance and dissolving the interaction between the locking protrusion 33 and the corresponding feature on the outside surface of the wing housing.

The embodiment according to FIG. 3 also has two tension strips 44 fixed 36 by co-molding with their end portions 45, 47 to the two jaws 34, 36, for biasing the jaws 34, 36 as described above.

Figure 4:
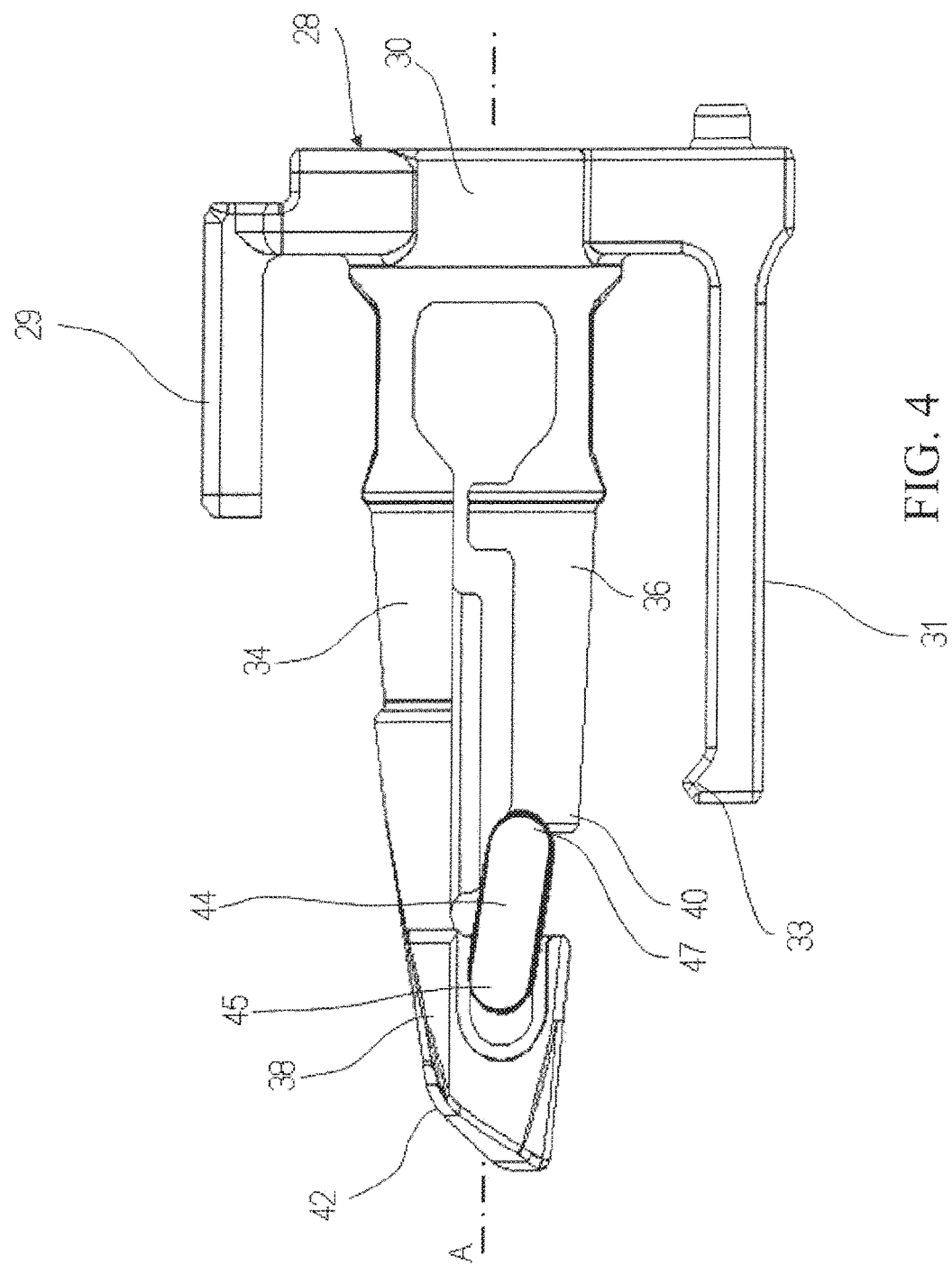
FIG. 4 shows a side view of a third embodiment of the needle safety device including a tension strip biased substantially in longitudinal direction.

FIG. 4 shows a further embodiment including two tension strips 44. The shape and structure of the needle safety device 28 is similar to the embodiment according to FIG. 3. However, the tension strips 44 of this embodiment are fixed by co-molding with their end portions 45, 47 to the head portions 38, 40 of the two jaws 34, 36 such that the tension strips 44 are biased substantially in longitudinal direction. In other words, as shown in FIG. 4 the tension strips 44 run in longitudinal direction in the relaxed state, i.e. along the longitudinal center axis of the needle safety device 28. When the jaws 34, 36 are spread apart due to the needle shaft extending therebetween (not shown), of the tension strips 44 are stretched and run inclined to the longitudinal center axis.

Figure 5:
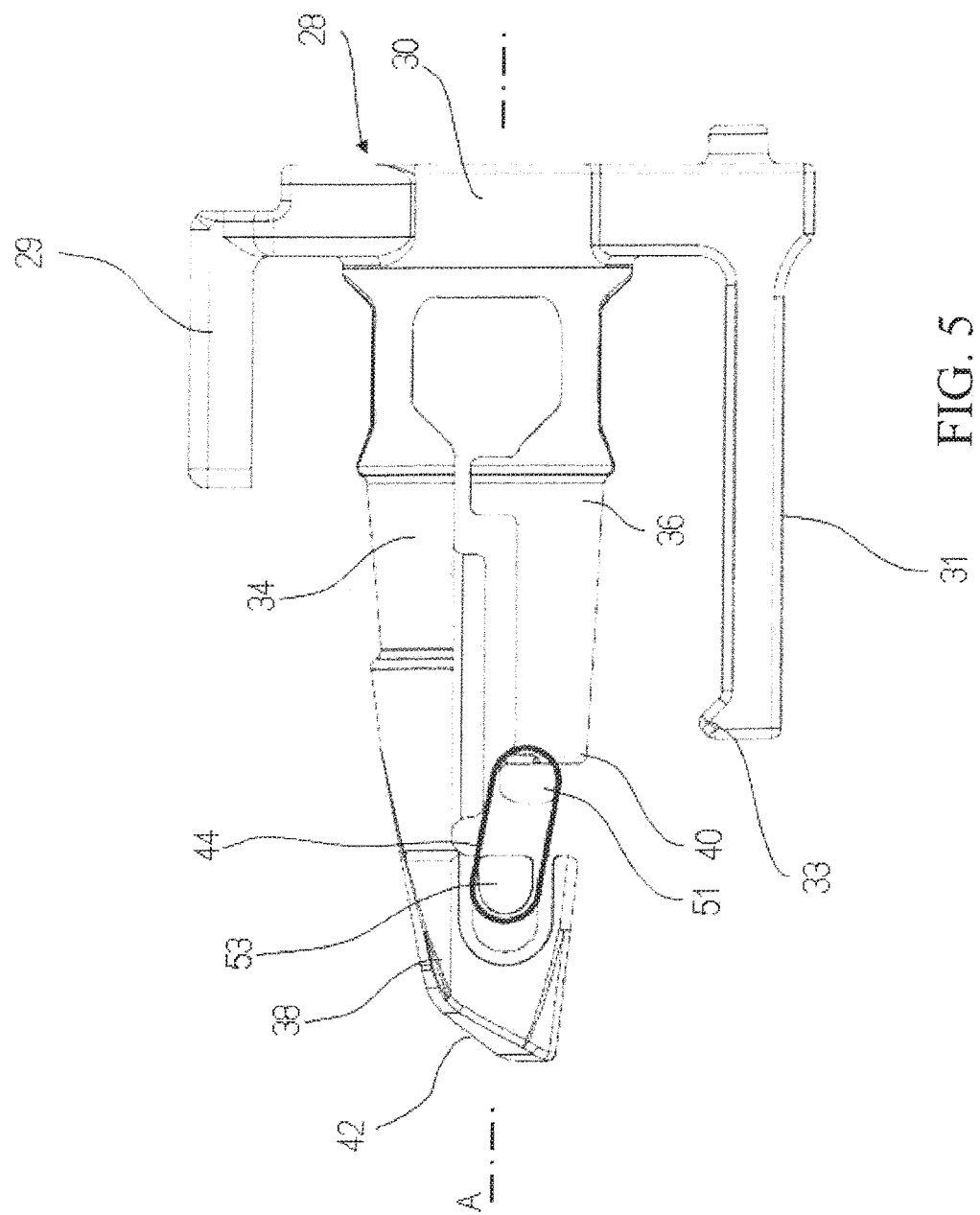
FIG. 5 shows a side view of a fourth embodiment of the needle safety device including a tension ring biased substantially in longitudinal direction.

FIG. 5 shows a further embodiment including two tension rings 44. The tension rings 44 are annular elements, e.g. 0-rings, formed from elastic material such as rubber or the like. On each head portion 38, 40 of the two jaws 34, 36 hook-like projections 51, 53 are integrally formed, which protrude from the needle safety device 28 in lateral opposite directions. The tension rings 44 are hooked on these projections 51, 53 and biased there between. The functioning is similar to that of the tension strips 44 shown in FIG. 4.

Figure 6:
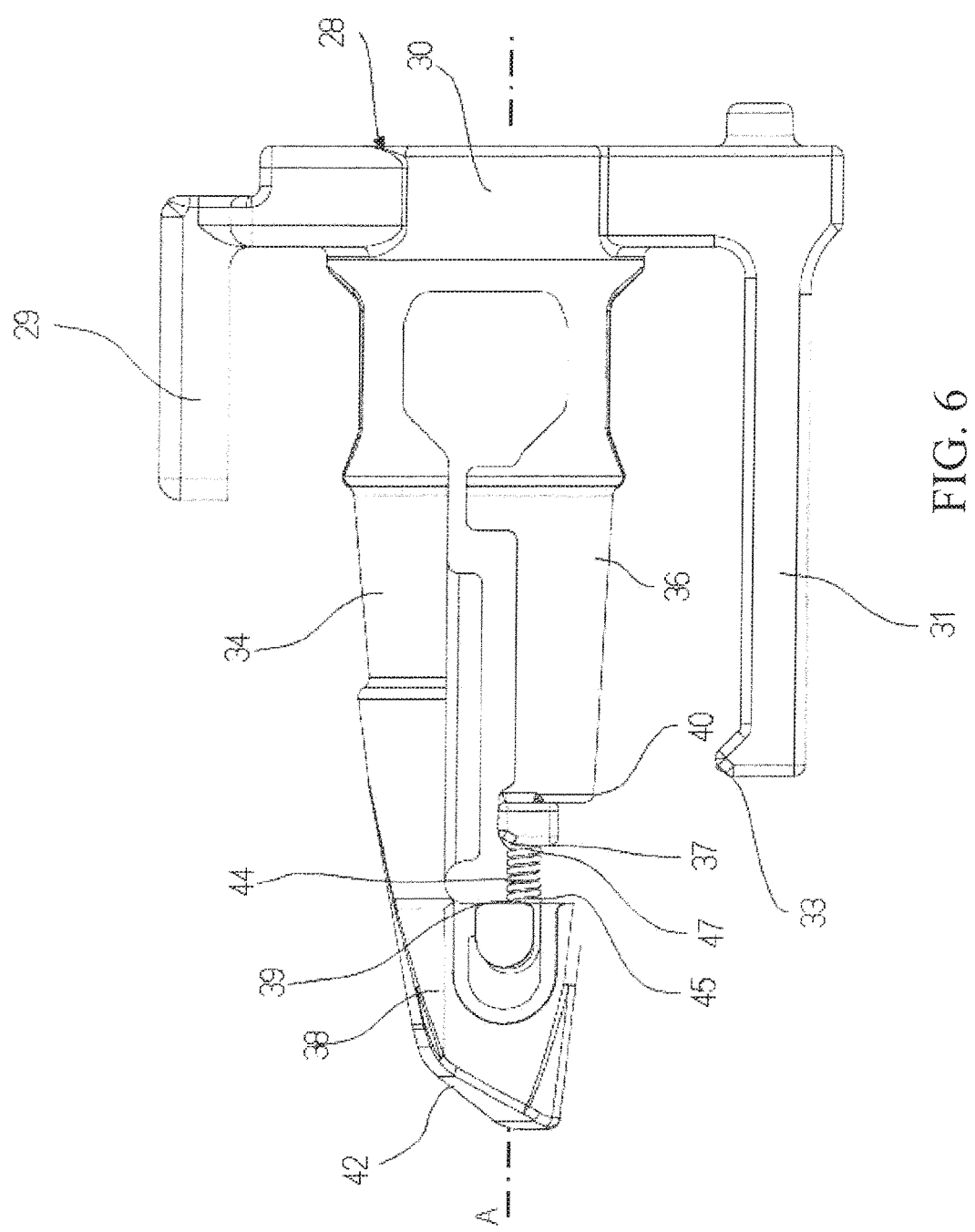
FIG. 6 shows a side view of a fifth embodiment of the needle safety device including a tension spring biased substantially in longitudinal direction.

FIG. 6 shows a further embodiment including at least one tension spring 44. The tension spring 44 is fixed with its end portions 45, 47 to opposite sides 37, 39 of the two head portions 36, 38 of the two jaws 34, 36. The tension spring 44 is formed as the coil spring which is stretched and expanded against a restoration force when the two jaws 34, 36 are spread by the needle shaft extending therebetween (not shown). The fixation of the end portions 45, 46 of the tension spring 44 on the opposite surfaces 37, 39 can be achieved by press-fitting the end portions 45, 47 into corresponding recesses in these surfaces 37, 39, by hook-like connections, by using an adhesive the end portions or by combinations thereof.

REFERENCE NUMERAL LIST

10: wing housing
12: main body
14: distal end
16: proximal end
17: catheter
18: port
20: wing
22: chamber
24: needle
26: enlargement
28: needle safety device
29: side arm
30: base portion
31: side arm
32: locking projection
34: first jaw
36: second jaw
37: surface
38: head portion
39: surface
40: head portion
42: angled end section
44: tension strip, tension ring, tension spring
45: end portion
46: link
47: end portion
48: annular protrusion
50: locking shoulder
51: hook-like protrusion
52: recess
53: hook-like protrusion
54: locking protrusion
56: needle tip
58: additional material
60: recess

What is claimed is:

1. A needle safety device for a medical device, the needle safety device comprising:
   a base portion having a bore extending along a longitudinal center axis therethrough for receiving a needle having a needle tip and a needle shaft;
   two opposing jaws extending from the base portion generally in the axial direction and each having a head portion in the region of its free end, wherein a projection extends outwardly from the head portion of one of said jaws; and
   an elastic element constructed separate from the jaws and configured to be mounted on the projection extending outwardly from the head portion of the one of said jaws and connected to the head portion of the other of said jaws, wherein
   the needle safety device includes a locking projection for securing the needle safety device to the medical device, wherein the elastic element and the jaws are configured such that the jaws are capable of being spread apart against a restoring force of the elastic element that is provided in an axial direction on one side of the needle shaft, and also providing a restoring force transverse to the axial direction on another side of the needle shaft in order to hold the needle tip within the needle safety device as the needle is pulled through the needle safety device, and wherein
   the transverse force and/or the axial force is also provided on the jaws when the needle is not within the needle safety device.

2. The needle safety device in accordance with claim 1, wherein the elastic element comprises rubber or silicone.

3. The needle safety device in accordance with claim 1, wherein the elastic element comprises a tension ring or tension strip or tension spring mounted to the jaws, respectively.

4. The needle safety device in accordance with claim 3, wherein the tension ring is mounted to a mounting structure provided on each of the jaws.

5. The needle safety device in accordance with claim 4, wherein the mounting structure comprises a projection, a hook, and/or a mounting recess.

6. The needle safety device in accordance with claim 1, wherein the elastic element comprises an elastic ring mounted on one side of each of the jaws.

7. The needle safety device in accordance with claim 1, wherein only one elastic element is provided on only one side of the jaws.

8. The needle safety device in accordance with claim 1, wherein the elastic element comprises an elastic ring connected to extensions extending in a transverse axial direction from a side of the jaws.

9. The needle safety device in accordance with claim 1, wherein at least one of the jaws has an angled end section at its free end, which extends towards the other one of the jaws in a direction generally perpendicular to the axial direction.

10. An intravenous catheter apparatus comprising:
a needle having a needle tip; and
a needle safety device in accordance with claim 1, slidably arranged on the needle for protecting the needle tip, wherein the bore of the needle safety device is adapted to a principal outer profile of the needle.

11. An intravenous catheter apparatus in accordance with claim 10, wherein a locking protrusion for engaging with the needle safety device is formed on an inner or outer surface of a catheter hub of the intravenous catheter apparatus.

12. The intravenous catheter apparatus in accordance with claim 11, wherein said locking protrusion is annular.

13. The intravenous catheter apparatus in accordance with claim 11, wherein a length of an angled end section is selected such that the angled end section is supported on the needle when the needle extends all the way through the needle safety device, thereby spreading the jaws apart far enough for a shoulder of the head portion of the jaw having the angled end section to engage with a housing of the medical device for securing the needle safety device in the housing.

14. The safety device of claim 1, wherein said elastic element acts alone in providing said restoring force to the jaws during normal operation.

15. A needle safety device for a medical device, the needle safety device comprising:
a base portion having a bore extending along a longitudinal center axis therethrough for receiving a needle having a needle tip and a needle shaft;
two opposing jaws extending from the base portion generally in the axial direction and each having a head portion in the region of its free end; and
an elastic element constructed separate from the jaws and configured to be mounted on the jaws, wherein
the needle safety device includes a locking projection for securing the needle safety device to the medical device, wherein the elastic element and the jaws are configured such that the jaws are capable of being spread apart against a restoring force of the elastic element that is provided in an axial direction on one side of the needle shaft, and also providing a restoring force transverse to the axial direction on another side of the needle shaft in order to hold the needle tip within the needle safety device as the needle is pulled through the needle safety device, and wherein
the transverse force and/or the axial force is also provided on the jaws when the needle is not within the needle safety device, and wherein
the elastic element comprises a coil spring mounted on an end of one of the jaws.

16. The needle safety device in accordance with claim 15, wherein the coil spring has ends fixed to opposing surfaces of each of the jaws, respectively.

17. A needle safety device for a medical device, the needle safety device comprising:
a base portion having a bore extending along a longitudinal center axis therethrough for receiving a needle;
two opposing jaws extending from the base portion generally in the axial direction and each having a head portion in the region of its free end and;
an elastic element constructed separate from the jaws and configured to be connected to an end or to a projection extending from the end of one of the jaws, wherein
the needle safety device includes a locking projection for securing the needle safety device to the medical device, wherein the elastic element is a separate component comprising a material different than the material comprising the jaws that is mounted and secured to an outer surface of the jaws or to a part protruding therefrom, said elastic element being arranged with the jaws in a non-surrounding manner lateral to the center axis in a region between the base portion and the head portions, wherein the elastic element and the jaws are configured such that the jaws are capable of being spread apart against a restoring force of the elastic element that is provided in an axial direction on one side of the needle shaft, and also providing a restoring force transverse to the axial direction on another side of the needle shaft in order to allow the needle received in the bore to extend all the way through the needle safety device while holding the needle tip within the needle safety device as the needle is pulled through the needle safety device.

18. The safety device of claim 17, wherein said elastic element acts alone in providing said restoring force to the jaws during normal operation.

19. The needle safety device in accordance with claim 17, wherein the elastic element comprises a tension ring or tension spring mounted to the jaws, respectively.

20. The needle safety device in accordance with claim 19, wherein the tension ring or tension spring is mounted to a mounting structure provided on each of the jaws.

21. The needle safety device in accordance with claim 20, wherein the mounting structure comprises a projection, a hook, and/or a mounting recess.

22. The needle safety device in accordance with claim 17, wherein the elastic element comprises an elastic ring connected to extensions extending in a transverse axial direction from a side of the jaws.

23. The needle safety device in accordance with claim 17, wherein at least one of the jaws has an angled end section at its free end, which extends towards the other one of the jaws in a direction generally perpendicular to the axial direction.

24. A needle safety device for a medical device, the needle safety device comprising:
a base portion having a bore extending along a longitudinal center axis therethrough for receiving a needle having a needle tip and a needle shaft;
an elastic element; and
two opposing jaws extending from the base portion generally in the axial direction and each having a head portion in the region of its free end, wherein the needle safety device includes a locking projection for securing the needle safety device to the medical device, wherein the elastic element is connected to an end or to a projection extending from the end of one of the jaws, and further wherein the elastic element is connected to a portion underneath an end or to a projection extending from underneath an end of another one of the jaws, and still further wherein the elastic element and the jaws are configured such that the jaws are capable of being spread apart against a restoring force of the elastic element that is provided in an axial direction on one side of the needle shaft, and also providing a restoring force transverse to the axial direction on another side of the needle shaft in order to hold the needle tip within the needle safety device as the needle is pulled through the needle safety device.

* * * * *